United States Patent [19]
Wallace et al.

[11] Patent Number: 6,059,795
[45] Date of Patent: May 9, 2000

[54] MANEUVERABLE FETAL VACUUM EXTRACTION FOR USE WITH MALPRESENTING FETUS

[75] Inventors: William Dean Wallace; Richard A. Dixon; Steven R. Smith, all of Salt Lake City; Christopher A. Cutler, Centerville, all of Utah

[73] Assignee: Clinical Innovations, Murray, Utah

[21] Appl. No.: 09/203,003

[22] Filed: Nov. 30, 1998

Related U.S. Application Data

[63] Continuation-in-part of application No. 09/075,448, May 8, 1998.

[51] Int. Cl.[7] .................................................. A61B 17/42
[52] U.S. Cl. ........................................ 606/123; 606/122
[58] Field of Search .................................... 606/123, 122, 606/119, 106, 127, 124; 604/74, 149

[56] References Cited

U.S. PATENT DOCUMENTS

| | | | |
|---|---|---|---|
| 2,194,989 | 3/1940 | Torpin | 128/361 |
| 2,702,038 | 2/1955 | Uddenberg et al. | 128/361 |
| 2,917,050 | 12/1959 | Kenyon | 128/361 |
| 3,202,152 | 8/1965 | Wood et al. | 128/361 |
| 3,207,160 | 9/1965 | Heyns | 128/361 |
| 3,612,722 | 10/1971 | Neward | 417/63 |
| 3,765,408 | 10/1973 | Kawai | 128/352 |
| 3,782,385 | 1/1974 | Loyd | 128/281 |
| 3,794,044 | 2/1974 | Vennard et al. | 128/352 |
| 5,019,086 | 5/1991 | Neward | 606/123 |
| 5,071,403 | 12/1991 | Larsson | 604/74 |
| 5,224,947 | 7/1993 | Cooper et al. | 606/123 |
| 5,281,229 | 1/1994 | Neward | 606/123 |
| 5,395,379 | 3/1995 | Deutchman et al. | 606/123 |
| 5,693,058 | 12/1997 | Cavanagh et al. | 606/123 |
| 5,713,909 | 2/1998 | Lindsay | 606/123 |
| 5,803,926 | 9/1998 | Neward | 606/122 |
| 5,810,840 | 9/1998 | Lindsay | 606/123 |
| 5,935,136 | 8/1999 | Hulse et al. | 606/123 |

FOREIGN PATENT DOCUMENTS

| | | |
|---|---|---|
| 1123432 | 2/1962 | Germany. |
| 3138-589 | 7/1975 | Germany. |
| 61B17/42 | 3/1955 | Sweden. |
| WO89/06112 | 7/1989 | WIPO. |

OTHER PUBLICATIONS

The Venthouse; The Obstetric Vacuum Extractor, J.A. Chalmers, London, 1971, 13 pages.

Anwendung des Extraktors in der Geburtshilfe; Von V. Finderle, Apr. 1952, pp 16 and 226–230.

Handbook of Vacuum Extraction in Obstetric Practice, Aldo Vacca, Edward Arnold, a division of Hodder & Stoghton, 1992, pp. 1–27.

(List continued on next page.)

*Primary Examiner*—Gary Jackson
*Assistant Examiner*—Kevin Truong
*Attorney, Agent, or Firm*—Workman, Nydegger & Seeley

[57] ABSTRACT

The fetal contact cup portion of a fetal vacuum cup has an inside surface which, when applied to a fetal head, defines a fetal contact chamber with the fetal head. One end of a tube is attached to the fetal contact cup such that vacuums within the tube are applied within the fetal contact cup. The other end of the tube can be connected with a vacuum source and with a handle. The tube has a very small average outside diameter compared with conventional fetal vacuum tubes. Thus the fetal vacuum cup is less intrusive during insertion and is more easily maneuverable, especially when the fetus is malpresenting in, for example, the high occipitoposterior or high occipitolateral positions. The average outside diameter of the tube may be, for example, less than 150 mils and has a finger grip that compression fits into a recess defined by the outer surface of the fetal contact cup for a lower profile and easy positioning of the fetal contact cup onto the flexion point of the fetal head. During traction, however, the finger grip pulls out of the recess for more efficient traction. The fetal contact cup may have a soft lip for contacting the fetal head. Furthermore, the tubing may have markings to indicate proper positioning of the fetal vacuum cup over the flexion point.

14 Claims, 12 Drawing Sheets

OTHER PUBLICATIONS

CMI Obstetrical Vacuum Delivery Kit product information, Aug. 1995, Redmond, Oregon, 34 pages.

Handbook of Vacuum Extraction in Obstetric Practice, Aldo Vacca, pp. 55–62.

Chapter 9, Vacuum Delivery, Operative Obstetrics, pp. 173–189.

Arvind S. Moolgaoker, MD, Syed O.S. Ahamed, and Peter R. Payne, A Comparison of Different Methods of Instrumental Delivery Based on Electronic Measurements of Compression and Traction, Feb. 19, 1997, pp. 1–4.

6,059,795

MANEUVERABLE FETAL VACUUM EXTRACTION FOR USE WITH MALPRESENTING FETUS

CROSS-REFERENCE TO RELATED APPLICATIONS

This application is a continuation in part of U.S. patent application Ser. No. 09/075,448, entitled "Hand-Held Fetal Vacuum Extractor Having an Integrated Pump and Handle", filed May 8, 1998, which is incorporated herein by reference in its entirety.

BACKGROUND OF THE INVENTION

The safe propagation of the human race is fundamental to the well being of our society. One need not be a parent to realize the importance of improved medical devices and methods for safely delivering a fetus.

In vaginal deliveries, the fetus is delivered through the birth canal after the cervix of the mother has fully dilated and effaced. Passing the fetus through the birth canal requires that the vaginal muscles be forced to stretch because the fetal head is much larger than the birth canal under normal circumstances.

Some stretching force is applied to the vaginal tissues by the mother herself. The involuntary contractions of the uterus during labor push the fetus (typically the fetal head) into the birth canal thereby stretching the vaginal tissues of the birth canal wall. The stretching force of these involuntary uterine contractions is combined with the stretching force caused by voluntary contractions of the mother's abdominal muscles as the mother tries to push the fetus out of the uterus.

Often the forces described above are not strong enough or are not medically advisable to use in extracting the fetus. Supplementary force may be applied, for example, in conditions of dystocia (i.e., slow or difficult labor or delivery), uterine inertia, maternal exhaustion, maternal distress, or fetal distress.

Supplementary force may be applied with conventional forceps which grasp the fetal head for traction through the birth canal. However, forceps often cause injuries to the fetal head. Forceps also have an awkward rigid shape which often causes maternal discomfort. Thus, fetal vacuum extractors were developed.

In conventional vacuum-assisted deliveries, a fetal vacuum cup is applied to the fetal head so that the center of the cup corresponds as close as possible to the flexion point of the fetal head. Referring to FIG. 11, the "flexion point" 1101 is medically defined as being approximately three centimeters anterior (i.e., towards the fetal face) from the posterior fontanelle 1102 (i.e., the triangular soft spot on the back of the fetal head 1100) along the sagittal suture 1103 (i.e., mid-line). For clarity, the anterior fontanelle 1104 (i.e., the diamond-shaped soft spot on the top of the fetal head 1100) is also shown in FIG. 11.

The positioning of the center of the cup on the flexion point is important to a safe, relatively easy vacuum-assisted delivery. Traction applied along the pelvic axis from a properly positioned vacuum cup promotes proper fetal presentation as the fetus passes through the birth canal.

Often, the fetus malpresents such that the flexion point is pressed against the birth canal walls. For example, the fetus may be high in the birth canal and presenting in the occipitoposterior or occipitolateral positions (hereinafter "high occipitoposterior" and "high occipitolateral", respectively). Proper positioning of the fetal vacuum cup over the flexion point is difficult if the fetus is malpresenting because the vacuum cup must be inserted between the birth canal wall and the occiput. Thus, the centers of the fetal vacuum cups are often not properly applied over the flexion point of malpresenting fetuses.

The maneuverability of the fetal vacuum cup affects the correct application of the vacuum cup over the flexion point of a malpresenting fetus. Factors that affect maneuverability are 1) the depth and profile of the vacuum cup, 2) the diameter of the vacuum cup, and 3) the design of the vacuum cup with regard to the position and pliability of the suction tube.

Several fetal vacuum extractors might conceivably be applied to a malpresenting fetus such as the device described in U.S. Pat. No. 5,810,840 entitled "Vacuum Extractor". The '840 device includes a cup 1202 (FIG. 12) that has a flexible closed top end 1220. In an insertion position, the stem 1204 is angularly disposed relative to the vertical axis 1288 of the cup 1202 such that a portion of the stem 1204 is recessed into the flexible closed top end 1220 of the cup 1202, thereby facilitating insertion of the cup 1202 into the birth canal in the direction 1286. Although the folding of stem 1204 is useful for insertion into the birth canal, the flexible structure of cup 1202 may not be structurally rigid enough to hold its shape when compressed between the flexion point and the birth canal wall. Also, the profile of the cup 1202 is not small enough to easily insert between the birth canal wall and the flexion point. Even once the cup 1202 is in place with the stem 1204 recessed within the cup 1202, the stem 1204 tends towards its original unrecessed position, often detaching (i.e., prying up and popping off) the cup 1202 from the fetal head. Furthermore, the traction force, when applied at an oblique angle, also contributes to cup 1202 detachment.

Another device is disclosed in U.S. Pat. No. 5,019,086 entitled "Manipulable Vacuum Extractor for Childbirth and Method of Using the Same" and is shown in FIG. 13. The stem 1314 includes a flexible portion 1314c which allows the stem 1314 to bend towards the cup 1330 to facilitate insertion into the birth canal. A significant portion of stem 1314 extends perpendicular from the cup 1330 inhibiting insertion of cup 1330 between the flexion point and the birth canal walls. Cup 1330 also suffers from the same detachment issues discussed above for the '840 device but to a greater extent.

Several devices are lower profile but are quite complicated to use. A device described in U.S. Pat. No. 5,803,926 is shown in FIG. 14. Arms 1414 and 1416 are coupled with the sides of cup 1412 to allow easier insertion into the birth canal. The doctor applies traction and manipulates the fetus with arms 1414 and 1416. This device is complicated to operate since the doctor must manipulate the arms with both hands and must coordinate relative motion between arms 1414 and 1416. The doctor thus has no free hand to perform other tasks. This device also tends to lift up one edge of the cup more than the other, thus prying up and popping off the cup from the fetal head.

Another device commonly used for a malpresenting fetus is the Bird posterior cup device 1500 shown in FIG. 15. This device includes a cup 1501, a handle 1502 and a vacuum hose 1503. Though the profile of the device 1500 is relatively low, the handle 1502 and vacuum hose 1503 must be separately manipulated by the doctor. Furthermore, the insertion of the hose 1503 and parts of the handle 1502 into the birth canal can be intrusive and uncomfortable to the mother. Also, the handle 1502 and hose 1503 may interfere with each other when traction is applied.

Therefore, there is a need for a low-profile, easily operated fetal vacuum cup.

SUMMARY OF THE INVENTION

In accordance with the present invention, a fetal vacuum cup includes a fetal contact cup and a tube. The fetal contact cup has an inside surface which, when applied to a fetal head, defines a fetal contact chamber with the fetal head. One end of the tube is attached to the fetal contact cup such that vacuums within the tube are applied within the fetal contact cup. The other end of the tube can be connected with a vacuum source and with a handle.

The tube has a very small average outside diameter compared with conventional fetal vacuum tubes. Thus the fetal vacuum cup is less intrusive during insertion and is more easily maneuverable, especially when the fetus is malpresenting in, for example, the high occipitoposterior or high occipitolateral positions. In one embodiment, the average outside diameter of the tube is less than 150 mils (0.150 inches) and has a finger grip that compression fits into a recess defined by the outer surface of the fetal contact cup. This compression fitting allows for easy positioning of the fetal contact cup onto the flexion point of the fetal head. During traction, however, the finger grip pulls out of the recess for more efficient traction.

In accordance with the present invention, a fetal vacuum extractor is used by applying a fetal contact cup to a fetal head to define a fetal contact chamber. A vacuum is applied in the fetal contact chamber through a tube attached to the fetal contact cup. The tube has a small average outside diameter compared with conventional fetal vacuum tubes. Traction is applied to the fetal head by pulling on a handle that is coupled to the tube. In one embodiment, the traction forces may be primarily applied through a pulling member (e.g., a cable) threaded through the tube for preventing irreversible strain of the tube. The walls of the tube could also be extruded to contain a strong wire or nylon braided weave to give strength to the tube and yet still give the tube flexibility.

The principles of the present invention will best be understood in light of the following detailed description along with the accompanying drawings.

DETAILED DESCRIPTION OF THE INVENTION

Several elements in the following figures are substantially similar. Similar reference symbols are used to represent the same or similar elements.

Figure 1:
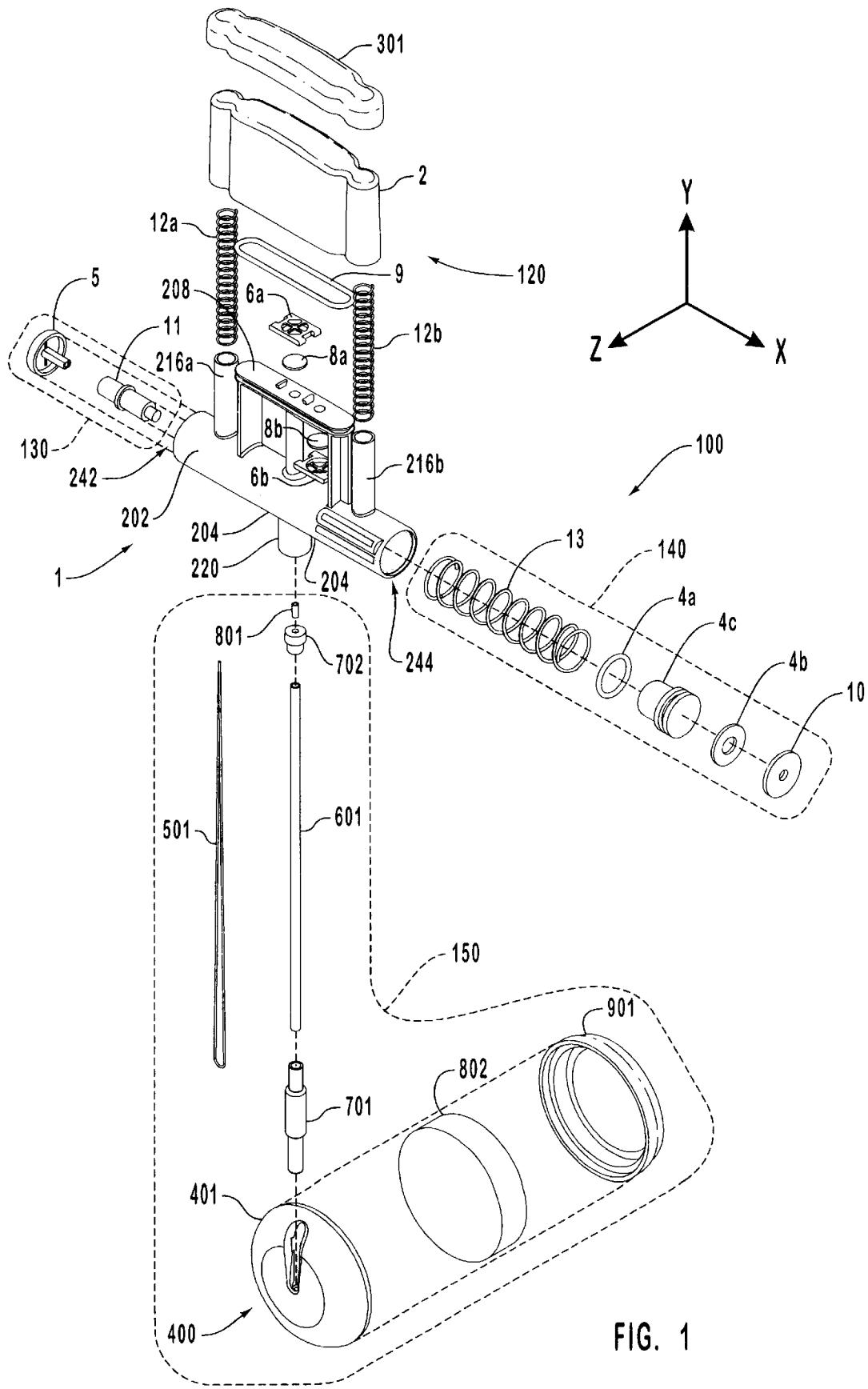
FIG. 1 is an exploded isometric view of one embodiment of a fetal vacuum extractor according to the invention.

In accordance with the present invention, a fetal vacuum extractor has a maneuverable low-profile fetal vacuum cup. FIG. 1 is an exploded isometric view of a fetal vacuum extractor 100 according to the invention. The extractor 100 includes five general components: a handle 1, a vacuum pump 120, a vacuum release 130, a vacuum indicator 140, and a low-profile vacuum cup 150. The pumping action of the extractor 100 is caused by the relative movement between handle 1 and palm chamber 2 (part of vacuum pump 120). Handle 1, vacuum pump 120, vacuum release 130 and vacuum indicator 140 may be those described in U.S. patent application Ser. No. 09/075,448, which is incorporated herein by reference.

Figure 2A:
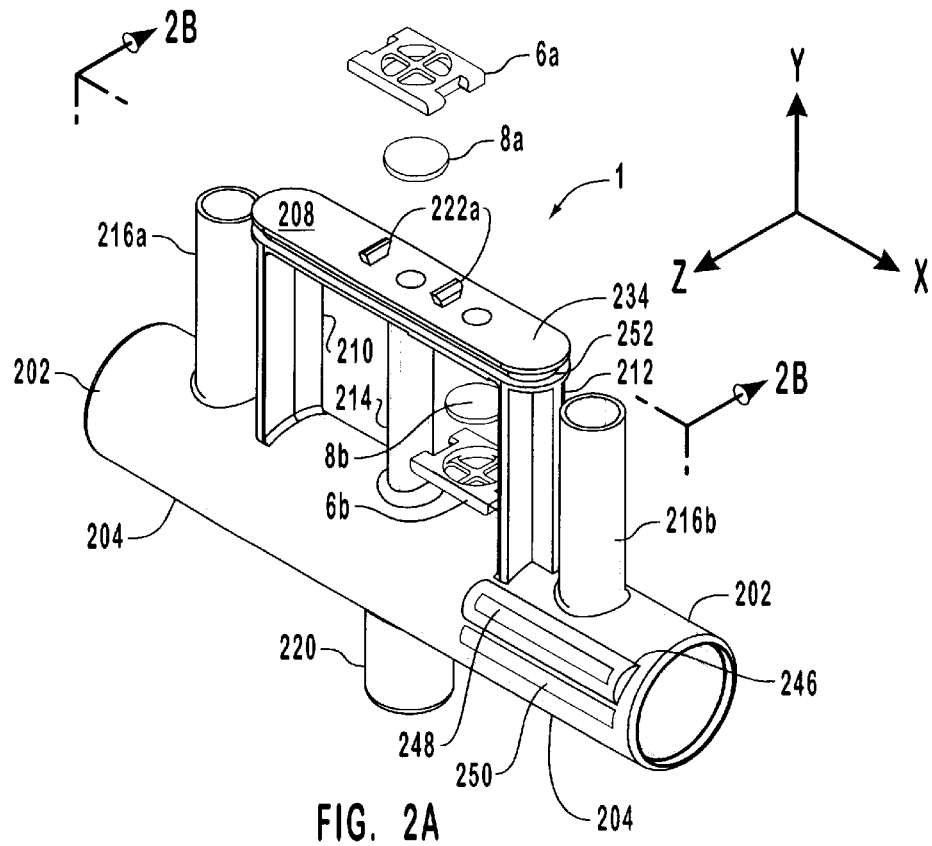
FIG. 2A is an isometric view of the handle of FIG. 1.

The structure of handle 1 is now described. FIG. 2A is an isometric view of handle 1. Handle 1 may be machined or molded and may be composed of polycarbonate or some other plastic. Handle 1 includes a main grip 202 having a finger contact surface 204. A piston 208 is part of vacuum pump 120 (FIG. 1) but is rigidly connected to handle 1. Piston 208 extends up from main grip 202 and is supported by side supports 210 and 212 and central support 214. Two spring guide columns 216a and 216b also extend up from main grip 202. A cup connector 220 extends down from main grip 202. Piston 208 has a top vacuum chamber surface 234 that defines upper ridges 222a for receiving a one-way vacuum flap valve 8a composed of, for example, silicone.

Figure 2B:
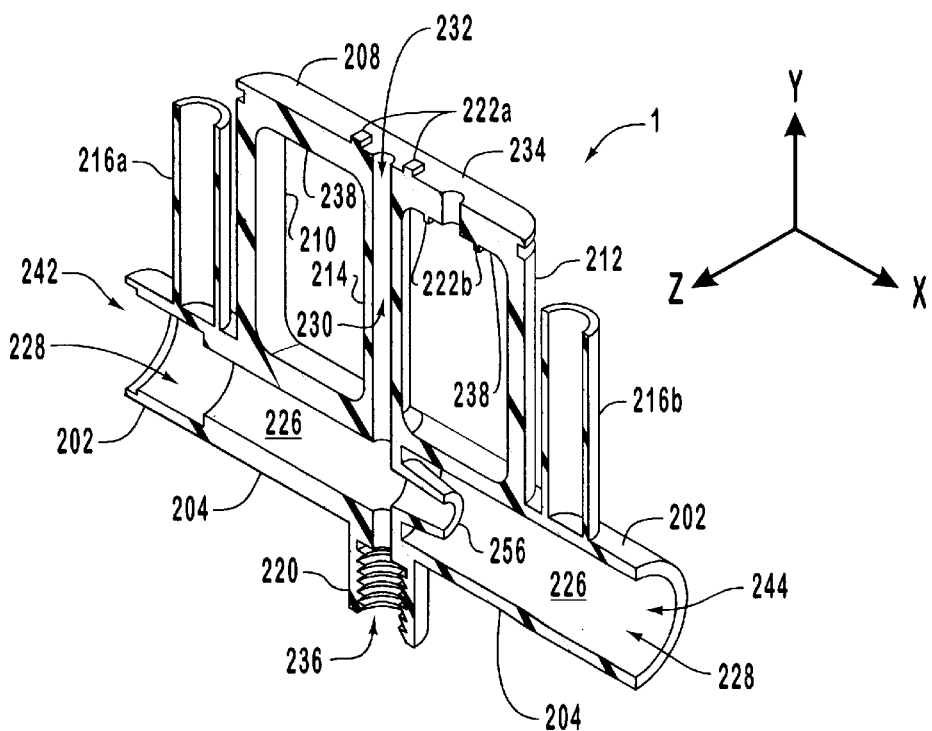
FIG. 2B is an isometric cross-sectional view of the handle of FIG. 2A along cross-section line 2B—2B of FIG. 2A.

FIG. 2B is an isometric cross-sectional view of handle 1 along cross-section line 2B—2B of FIG. 2A. FIG. 2B shows lower ridges 222b provided in a lower surface 238 of piston 208 for receiving a one-way exhaust flap valve 8b (FIG. 2A) composed of, for example, silicone. Main grip 202 is hollow having an inner surface 226 that defines a grip chamber 228. The grip chamber 228 is substantially sealed from atmosphere during operation as described in detail below. Central support 214 is hollow having an internal vacuum source channel 230 connecting grip chamber 228 to a hole 232 at the top vacuum chamber surface 234 of piston 208. Cup connector 220 is also hollow having an internal channel 236 having a top end fluidly coupled to grip chamber 228.

Handle 1 also includes a windowed gauge seating 246 (FIG. 2A) which may contain a metallic slider (not shown) such as a ferrous ball or flat plate that may be magnetic. The position of the metallic slider is visible through window 248 of gauge seating 246 so that an operator can correlate the position of the metallic slider with a label 250 to determine the vacuum pressure within grip chamber 228. Metallic slider interacts with vacuum indicator 140 (FIG. 1) as described in detail further below.

Figure 3A:
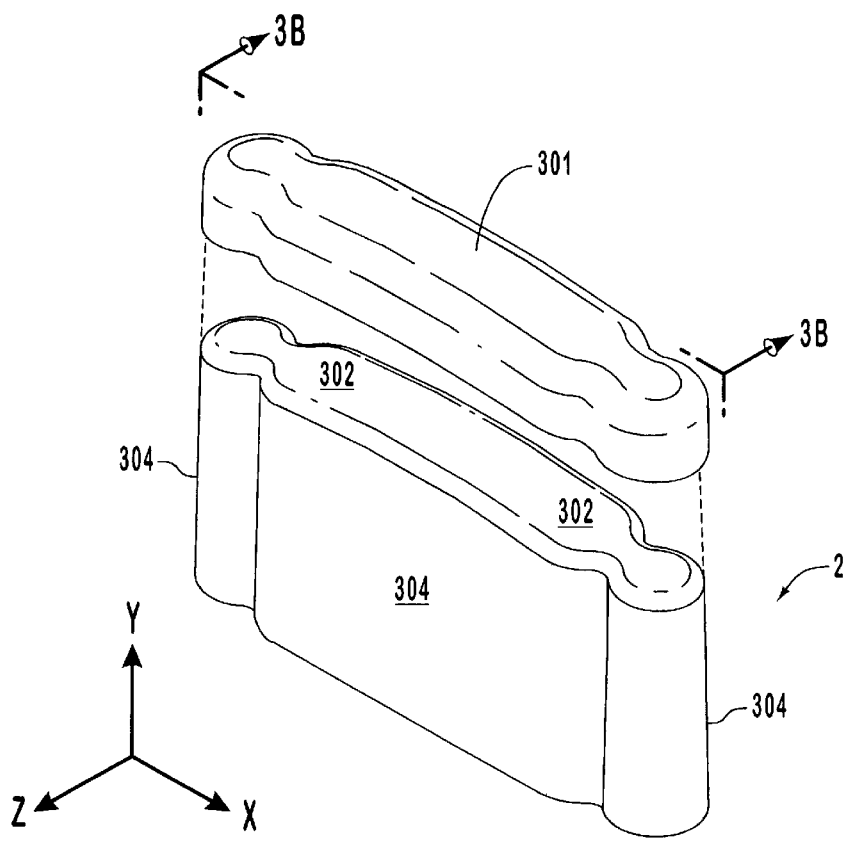
FIG. 3A is an isometric view of the palm chamber of FIG. 1.
Figure 3B:
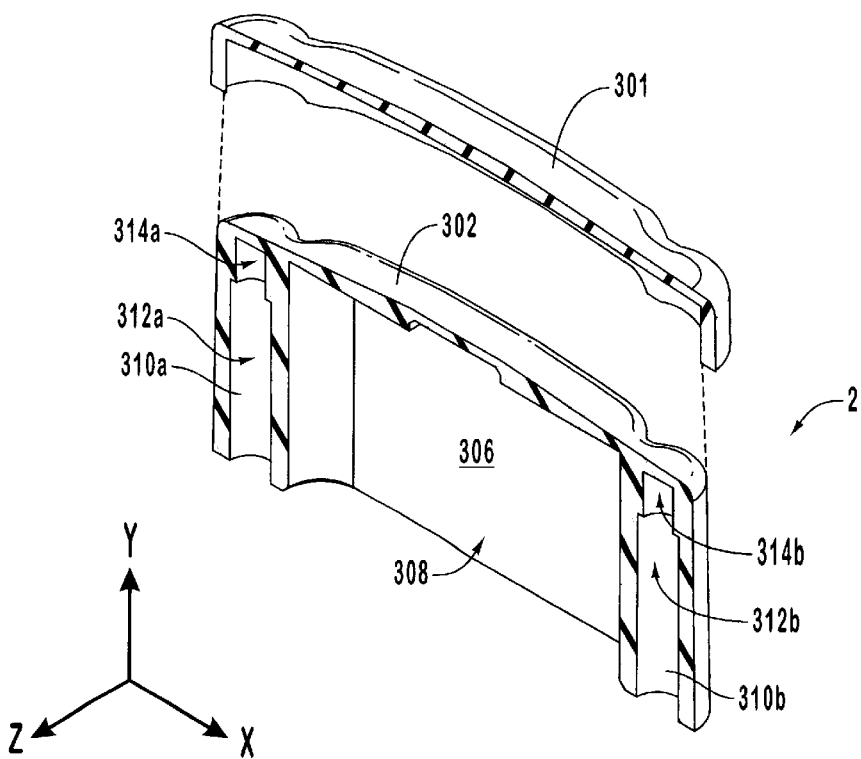
FIG. 3B is an isometric sectional view of the palm chamber of FIG. 3A along cross-section line 3B—3B of FIG. 3A.

The structure of palm chamber 2 is now described. Palm chamber 2 (part of vacuum pump 120) may be machined and/or molded, and may be composed of polyethylene or similar plastics. Palm chamber 2 is disposed over piston 208 and is described with reference to FIG. 3A and FIG. 3B. FIG. 3A is an isometric view of palm chamber 2 that is one integrated body having a palm contact surface 302 and a side surface 304. FIG. 3B is an isometric sectional view of palm chamber 2 along cross-section line 3B—3B of FIG. 3A. FIG. 3B shows that palm chamber 2 has an inner chamber surface 306 that, together with top chamber surface 234 of piston 208, defines a vacuum chamber 308. In one embodiment, palm chamber 2 has a palm cushion 301 (shown in exploded view in FIGS. 3A and 3B) covering the palm contact surface 302 for improved operator comfort and grip. Palm cushion 301 may be composed of, for example, polyvinyl chloride (PVC) or polyurethane of durometer measurement (i.e., a measure of softness) Shore A 60 durometer. Palm cushion 301 may be form molded to the shape of palm contact surface 302.

The structure of the interconnection between handle 1 and palm chamber 2 is now described. Referring again to FIG. 1, compression springs 12a and 12b (composed of, for example, music wire coated with a zinc plate to inhibit rust) are fitted into respective spring guide columns 216a and 216b. Compression springs 12a and 12b each have a spring constant of, for example, approximately 12 pounds per inch.

Vacuum and exhaust flap valves 8a and 8b are held by respective retainers 6a and 6b (FIGS. 1 and 2A). Vacuum and exhaust retainers 6a and 6b (composed of, for example, nylon or polycarbonate) are held by respective ridges 222a and 222b over respective flap valves 8a and 8b. A vacuum o-ring 9 (composed of, for example, silicone) is positioned along an outer periphery surface of piston 208 within groove 252 (FIG. 2A). Retainers 6a and 6b are composed of, for example, injection molded polycarbonate. Flap valves 8a and 8b may be punched from a thin sheet of silicone of durometer measurement Shore A 60 durometer. O-rings such as o-ring 9 are commonly available on the market.

The pumping action of vacuum pump 120 between handle 1 and palm chamber 2 is now described. When palm chamber 2 is compressed downward (in the negative y-direction parallel to the y-axis) with respect to handle 1, compression springs 12a and 12b are compressed within respective guide columns 216a and 216b by palm chamber 2 and handle 1. Thus, the extractor 100 is biased towards an uncompressed position. In the assembled, uncompressed position of the extractor 100, approximately three inches separate palm contact surface 302 of palm chamber 2 and finger contact surface 204 of main grip 202 such that the fingers of an average human hand can simultaneously grip main grip 202 at finger contact surface 204 and press on palm chamber 2 at palm contact surface 302. However, this distance can vary from one inch or less to five inches or more to accommodate different hand sizes and gripping preferences.

An operator pumps the extractor 100 by gripping the extractor 100 in its assembled, uncompressed position. The fingers of the operating hand are placed around main grip 202 while the palm of the operating hand is pressed against the palm contact surface 302 (or cushion 301) of the palm chamber 2. The operator squeezes the fingers towards the palm, thereby overcoming the bias of compression springs 12a and 12b and pressing palm chamber 2 towards handle 1.

The movement of piston 208 relative to palm chamber 2 forces piston 208 into vacuum chamber 308 and decreases the volume of vacuum chamber 308. The pressure within vacuum chamber 308 increases above the ambient pressure just enough to open the one-way exhaust flap valve 8b to exhaust the fluid from vacuum chamber 308 as palm chamber 2 is compressed. During compression, the pressure within vacuum chamber 308 only slightly rises above the ambient pressure enough to keep the one-way exhaust flap valve 8b open. Essentially, the pressure within vacuum chamber 308 is at ambient pressure when exhaust flap valve 8b is open. In the assembled, compressed position of the extractor 100, the distance between palm contact surface 302 of palm chamber 2 and finger contact surface 204 of main grip 202 is approximately two inches, but may vary from a half inch or less to four inches or more.

After the palm chamber 2 is compressed, the operator stops applying compressive force with the palm. Compression springs 12a and 12b then urge the extractor 100 towards its uncompressed position. The decompressing movement between piston 208 and palm chamber 2 causes the one-way vacuum flap valve 8a to open when the pressure of vacuum chamber 308 drops below the pressure within vacuum source channel 230. Thus the decompression movement causes fluid from grip chamber 228 to be vacuumed into vacuum chamber 308. Thus, one vacuum cycle is completed by the operator gripping and releasing handle 1 and palm chamber 2. The above pressing and release cycle may be repeated to apply stronger vacuums to grip chamber 228.

Vacuum release 130 is now described with reference to FIG. 1. A vacuum release 130 is provided in one longitudinal end 242 of main grip 202 to cap one end of grip chamber 228 (FIG. 2B). Vacuum release 130 includes a release valve 11 (composed of, for example, polyester, PVC, and/or stainless steel) which is first inserted into the end 242 of main grip 202. Release valve 11 may be, for example, part number BK333303S supplied by Bestak of Norfork, England. Vacuum release 130 also includes a release button 5 (composed of, for example, polycarbonate) which is inserted into the end 242 of main grip 202 over release valve 11. When release button 5 is pressed by, for example, the operator's thumb, fluid within grip chamber 228 communicates with the ambient environment through release valve 11, thereby releasing any vacuum within grip chamber 228.

Vacuum indicator 140 is now described with reference to FIG. 1. A vacuum indicator 140 is provided in the other longitudinal end 244 of main grip 202 and caps the other longitudinal end of grip chamber 228 (FIG. 2B). The vacuum indicator 140 includes a gauge spring 13 (composed of, for example, stainless steel), a gauge o-ring 4a (composed of, for example, silicone), a magnetic ring 4b, a piston 4c (composed of, for example, machined or molded polycarbonate), and a gauge cap 10 (composed of, for example, polycarbonate).

The oil lubricated gauge o-ring 4a is provided within a groove along the outer circumference of piston 4c so that gauge o-ring 4a seals the grip chamber 228 from the ambient environment at end 244. The magnetic ring 4b is composed of a magnetic material such as ceramic #8 (also commonly called ferrite) which has a chemical formula $BaFe_2O_3$ or $SrFe_2O_3$. For example, the magnetic ring may be 0.6 inches outer diameter and 0.4 inches inner diameter which are commonly available on the market. Other configurations of magnets may be substituted for magnetic ring 4b as will be apparent to those skilled in the art. The magnetic ring may be fastened (e.g., glued or press fit) into the outer end of piston 4c.

The piston 4c, and thus magnet ring 4b, is guided along a longitudinal direction (i.e., parallel to the x-axis) within grip chamber 228 in response to pressure differences between grip chamber 228 and the ambient pressure. For example, a strengthening vacuum causes the piston 4c to be pulled inwardly (in the negative x direction) into handle 1 thereby compressing spring 13. A weakening vacuum causes the piston 4c to be move outwardly (in the positive x direction). Thus, the position of piston 4c, and thus magnet ring 4b, is a function of the vacuum intensity within handle 1. The movement of magnetic ring 4b moves the metallic slider described above (which also may be magnetic) within gauge seating 246 so that the operator can determine the vacuum level by viewing the position of the metallic slider through window 248 on the outside of handle 1.

Vacuum release 130 and vacuum indicator 140 cap both ends 242 and 244 of grip chamber 228 so that when vacuum release 130 is not activated and vacuum flap valve 8a is closed, the grip chamber 228 and vacuum source channel 230 combination are sealed from atmosphere except through channel 236.

Although the above describes a specific handle and vacuum source, the vacuum cup described below can work with many different handles and sources of vacuum with at most minor modifications in the vacuum cup described below. Such modifications are intended to be within the scope of the present invention.

Vacuum cup 150 is now described. Referring to FIG. 1, vacuum cup 150 includes a fetal contact cup 400 (including cup top 401 and cup bottom 901) having a filter 802. Vacuum cup 150 also has a cable 501, a tube 601, a cup/handle connector 702, a finger grip 701 and a crimp 801. The structure of vacuum cup 150 may best be understood by describing the method of assembling vacuum cup 150.

Figure 4A:
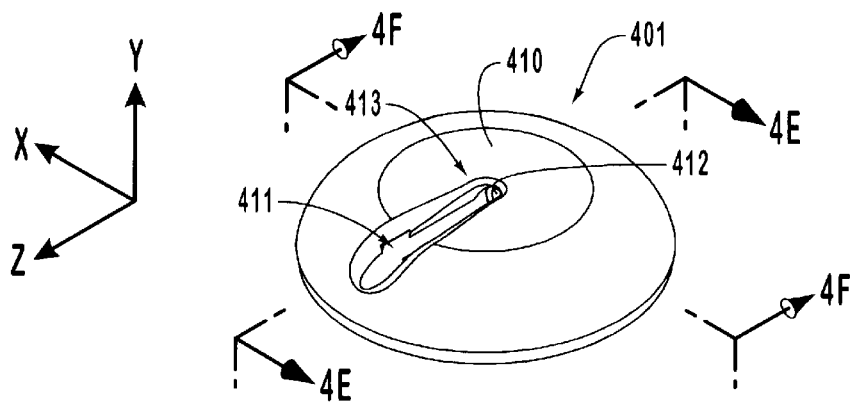
FIG. 4A is an isometric view of the cup top of FIG. 1.
Figure 4B:
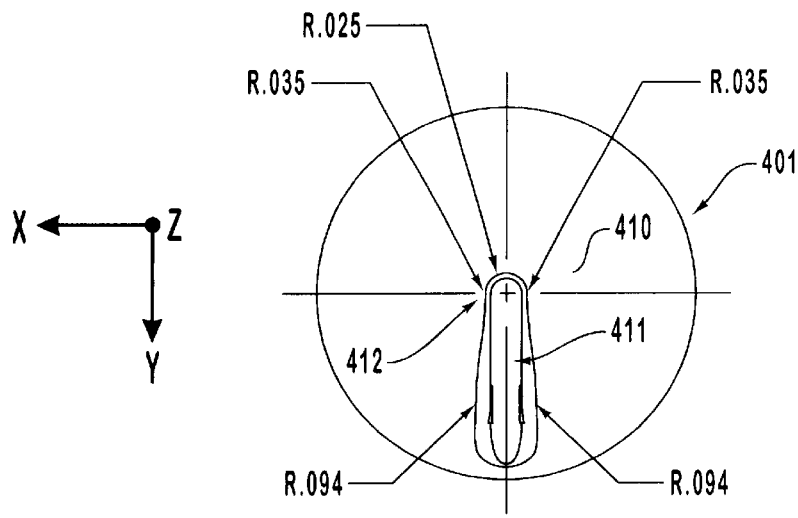
FIG. 4B is a top view of the cup top of FIG. 4A along the negative z direction.
Figure 4C:
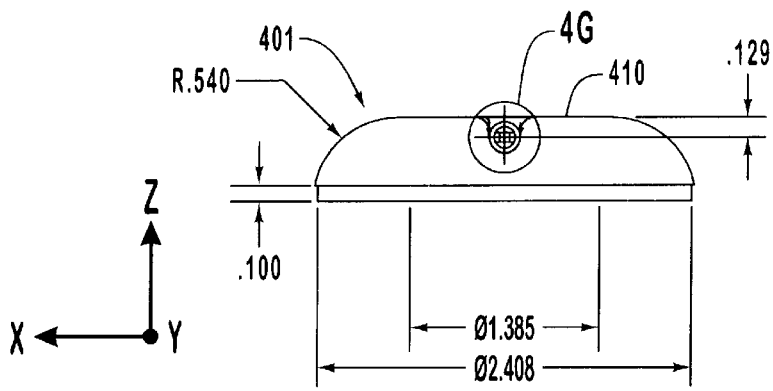
FIG. 4C is a side view of the cup top of FIG. 4A along the negative y direction.
Figure 4D:
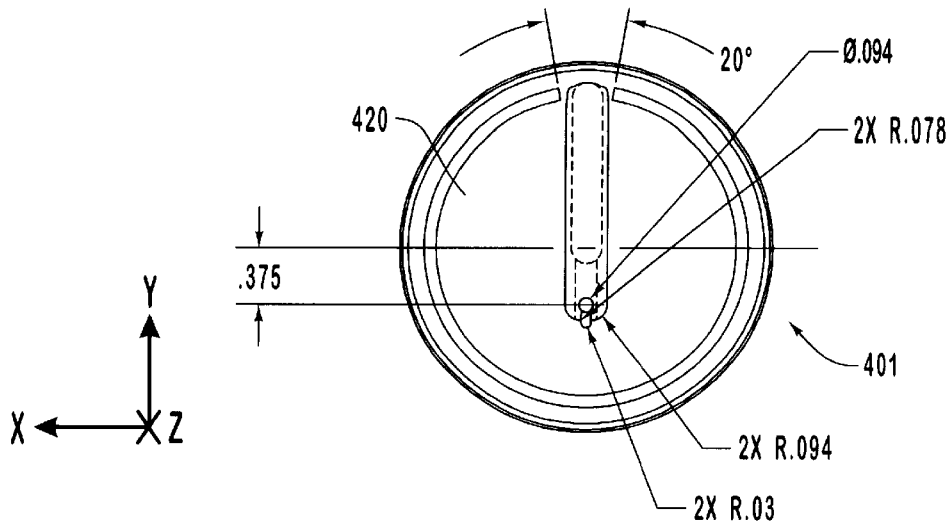
FIG. 4D is a bottom view of the cup top of FIG. 4A along the positive z direction.
Figure 4E:
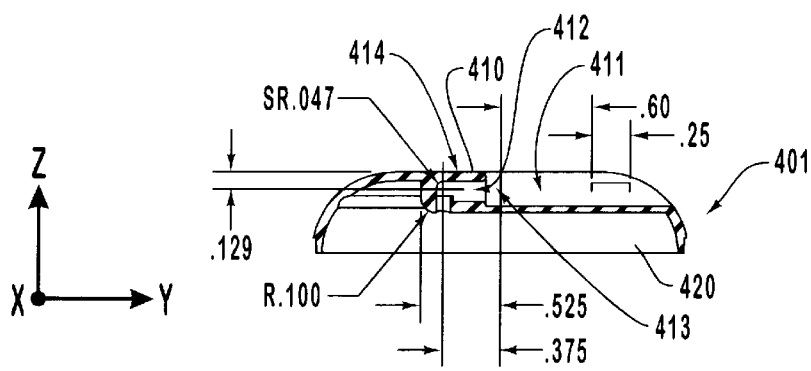
FIG. 4E is a cross-sectional view of the cup top of FIG. 4A along cross-section line 4E—4E of FIG. 4A.
Figure 4F:
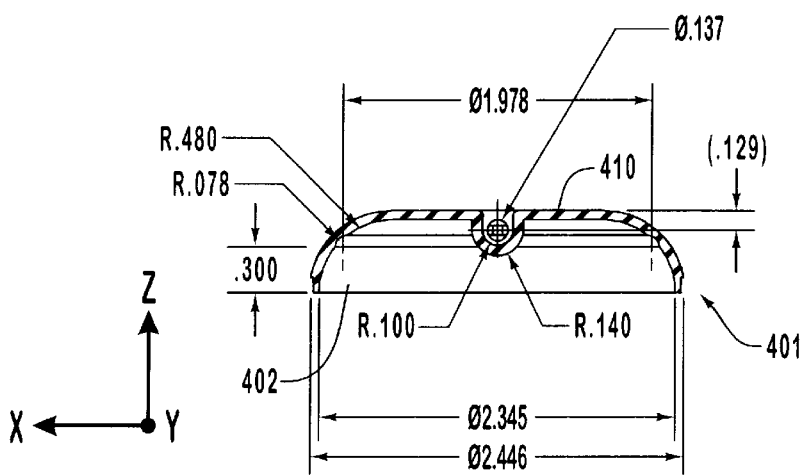
FIG. 4F is a cross-sectional view of the cup top of FIG. 4A along cross-section line 4F—4F of FIG. 4A.
Figure 4G:
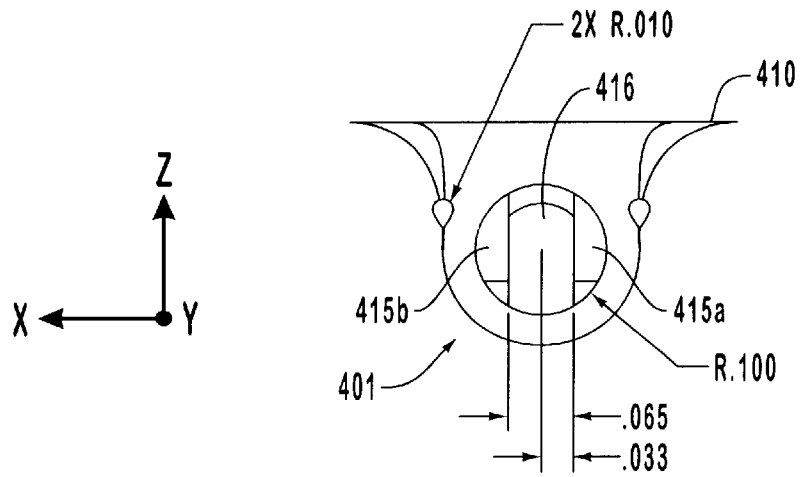
FIG. 4G is a detailed view of portion 4G of FIG. 4C.

FIG. 4A is an isometric view of cup top 401 which is injection molded and/or machined and is composed of a hard material such as polycarbonate. FIG. 4B is a top view of cup top 401 along the negative z direction. FIG. 4C is a side view of cup top 401 along the negative y direction. FIG. 4D is a bottom view of cup top 401 along the positive z direction. FIG. 4E and FIG. 4F are cross-sectional views of cup top 401 along respective cross-section lines 4E—4E and 4F—4F of FIG. 4A. FIG. 4G is a detailed view of portion 4G of FIG. 4C.

Cup top 401 is shaped like a flat topped dome having a top outer surface 410 and a bottom inner surface 420. Top surface 410 defines a recessed groove 411 and a thin tunnel 412 formed at an end 413 of the groove 411 as best seen in FIG. 4E. As best seen in FIG. 4G, two holes 415a and 415b are formed through cup top 401 at the end 414 of tunnel 412. A cable anchor 416 is also provided at the end 414 of tunnel 412. Cable anchor 416 may be, for example, a pillar extending from the top of tunnel 412 to the bottom of tunnel 412 as shown in FIG. 4G.

Figures 5A, 5B:
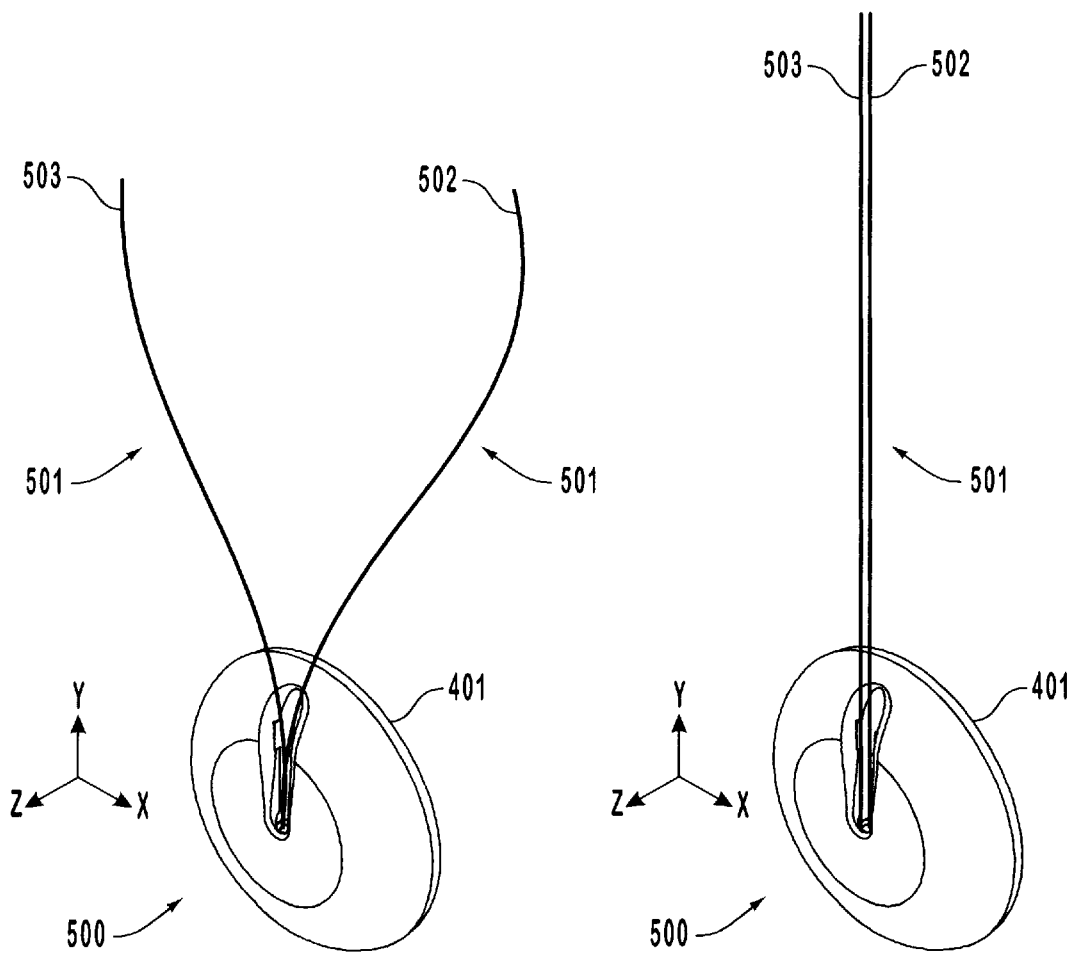
FIG. 5A is an isometric view of a portion of the vacuum cup of FIG. 1 after a first assembly step.
FIG. 5B is an isometric view of the portion of FIG. 5A with the cable in tension.

FIG. 5A shows a portion 500 of vacuum cup 150 after a first assembly step. Cable 501 is threaded down into tunnel 412, down through hole 415a, around cable anchor 416 returning back up through tunnel 412 via the other hole 415b resulting in portion 500. Thus, cable 501 is anchored to cup top 401 even if ends 502 and 503 of cable 501 are pulled as in FIG. 5B. Cable 501 may be composed of stainless steel and may be 28 mils in diameter.

Figure 6:
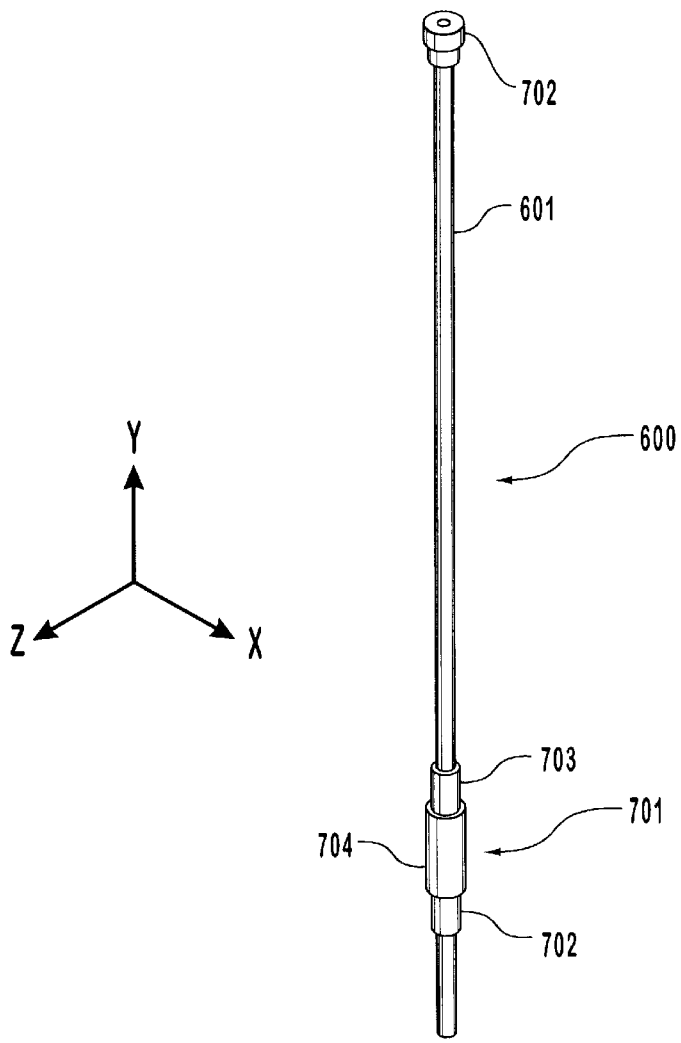
FIG. 6 is an isometric view of another portion of the vacuum cup of FIG. 1.
Figure 7A:
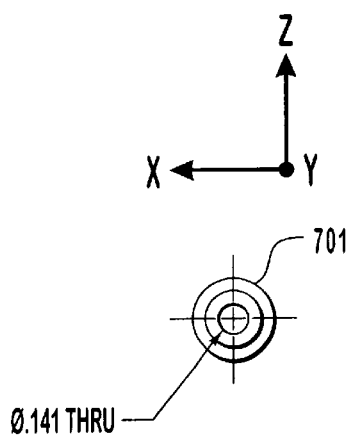
FIG. 7A is a front view of the finger grip of FIG. 6 along the negative y direction.
Figure 7B:
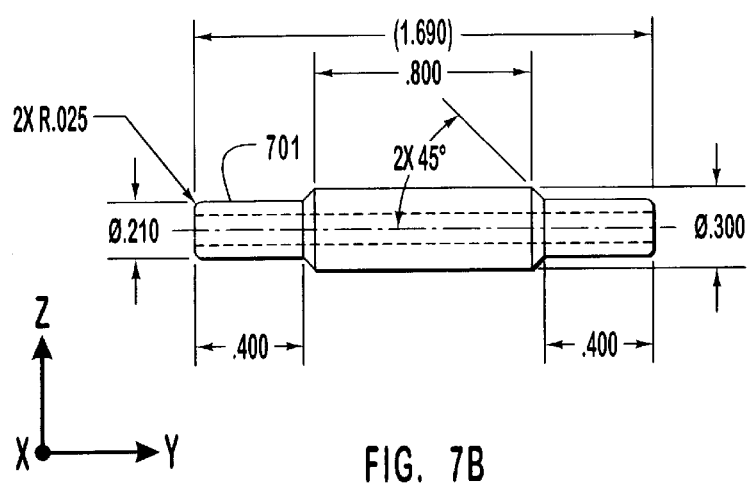
FIG. 7B is a side view of the finger grip of FIG. 6 along the negative x direction.

FIG. 6 shows another portion 600 of vacuum cup 150 after another assembly step. Tube 601, having an outside diameter of 140 mils, is inserted through a 141 mil inside diameter hole formed in finger grip 701. Front and side views of finger grip 701 are shown in FIGS. 7A, and 7B respectively. Tube 601 and finger grip 701 are solvent bonded together using, for example, methyl chloride which is drawn by capillary forces between tube 601 and finger grip 701. Tube 601 is also inserted into a cup/handle connector 702 having an inside diameter of approximately 141 mils. Tube 601 may be bonded to connector 702 using, for example, a conventional ultra violet adhesive which cures when exposed to ultra-violet light.

Tube 601 is composed of a flexible material such as, for example, extruded polyurethane or PVC, and has an inner diameter of, for example, 95 mils. Finger grip 701 may be composed of, for example, molded polyurethane or PVC, and has two end cylindrical portions 702 and 703 (outer diameter equals, for example, 210 mils) and a central cylinder 704 (outer diameter equals, for example, 300 mils). Cup/handle connector 702 may be composed of, for example, molded polycarbonate.

Tube 601 may have a marker measured 11 centimeters from the center of the cup. When the fetus is in the high occipitoposterior position and the fetal contact cup 400 is properly positioned, experts in the field have indicated that 11 centimeters separates the center of the fetal contact cup and the entrance to the birth canal viewable by the operator. Thus, if the fetal contact cup 400 is properly positioned, the marker should be positioned to be just viewable by the operator. Progress in labor can be measured by viewing how far the 11 cm marker extends outside the entrance to the birth canal. Conventionally, progress is determined by inserting a hand into the birth canal and feeling the fetal head. Thus, the 11 cm marker can avoid maternal discomfort since it can avoid the need to insert a hand into the birth canal to check fetal progress through the birth canal. Other markers may be provided as needed.

Figure 8A:
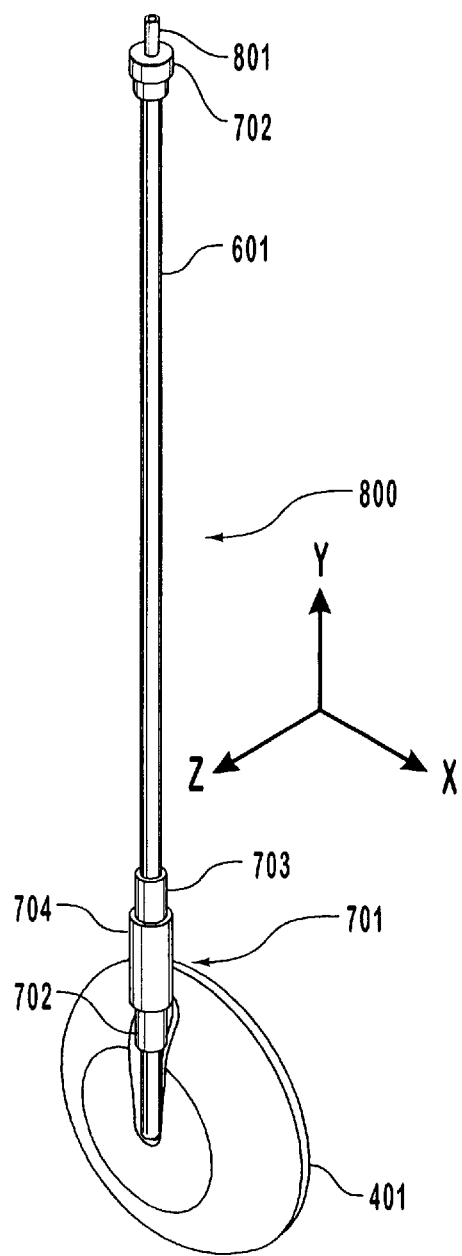
FIG. 8A is an isometric view of the assemble vacuum cup of FIG. 1 in an insertion position.
Figure 8B:
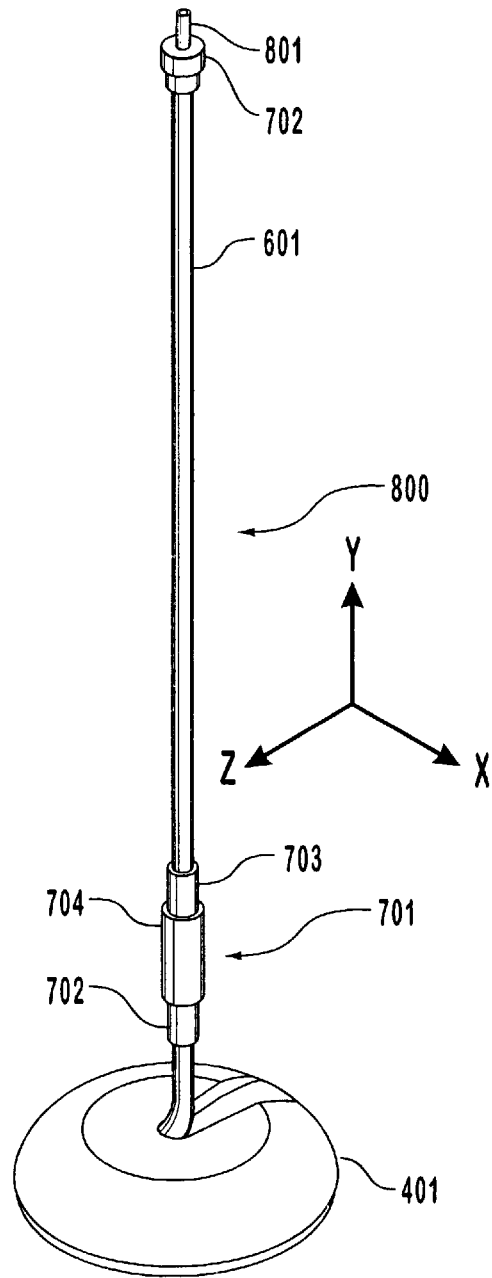
FIG. 8B is an isometric view of the assembled vacuum cup of FIG. 1 in a traction position.

FIG. 8A shows an assembled vacuum cup 150. Ends 502 and 503 of cable 501 (not visible in FIG. 8A) are threaded through tube 601 and tube 601 is inserted into tunnel 412 of cup top 401. Ends 502 and 503 are crimped in crimp 801 so that ends 502 and 503 of cable 501 are not pulled from cup/handle connector 702 if cup/handle connector 702 is pulled relative to cup top 401. Crimp 801 may be composed of, for example, brass. Tube 601 is adhered to cup top 401 within tunnel 412 using conventional adhesive. In the step of FIG. 8A, finger grip 701 should be positioned on tube 601 such that portion 702 of finger grip 701 is compression fitted into groove 411 when in the position shown in FIG. 8A (hereinafter, "the insertion position"). However, with some pulling, the portion 702 of finger grip 701 disengages with groove 411 resulting in the position shown in FIG. 8B (hereinafter, "the traction position").

A soft (e.g., Kraton) cup bottom 901 is adhesion bonded to cup top 401 using, for example, solvent bonding with methyl chloride. Alternatively, cup bottom 901 is insert molded to cup top 401 using insert molding. In other words, the harder cup top 401 is held in a mold while the softer cup bottom 901 is molded onto attaching portions of cup top 401.

Figure 9A:
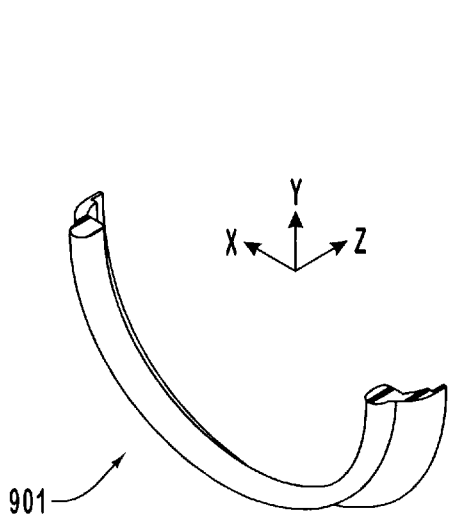
FIG. 9A is an isometric view of the cup bottom of FIG. 1 with a portion shown cut away for clarity.
Figure 9B:
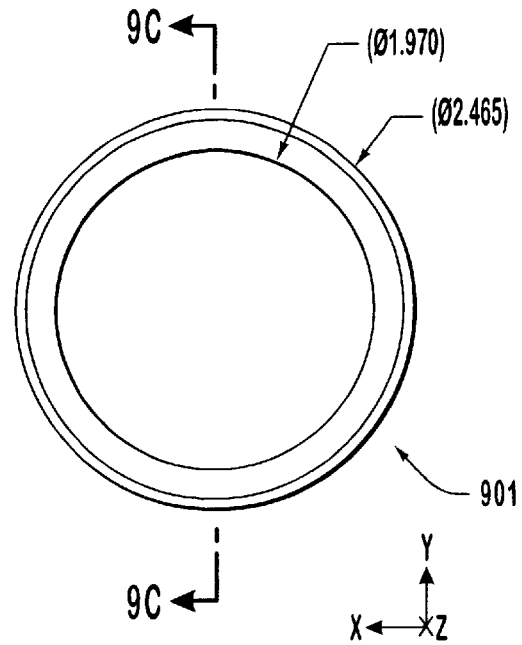
FIG. 9B is a bottom view of the cup bottom of FIG. 1 along the positive z direction.
Figure 9C:
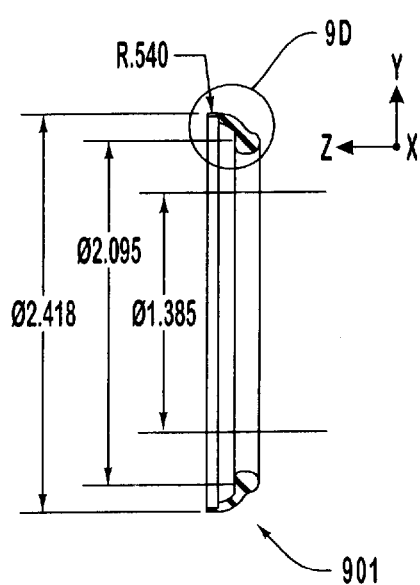
FIG. 9C is a cross-sectional view of the cup bottom of FIG. 1 along cross-section line 9C—9C of FIG. 9B.
Figure 9D:
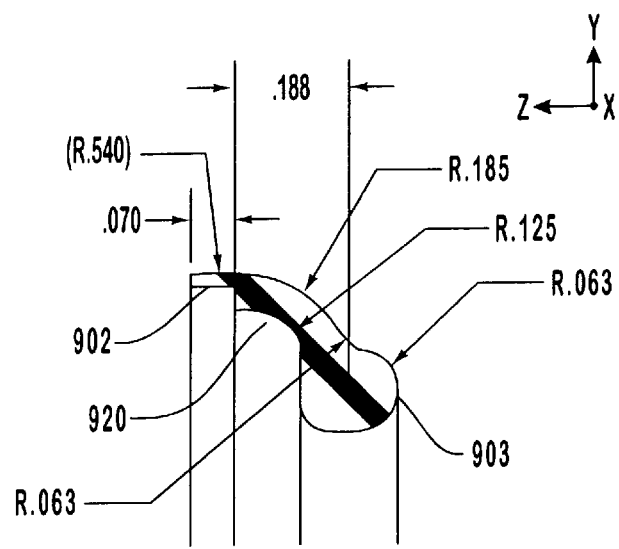
FIG. 9D is a detailed view of portion 9D of FIG. 9C.

FIG. 9A is an isometric view of cup bottom 901 with a portion cut away for clarity to show a cross-section of cup bottom 901. FIG. 9B is a bottom view of cup bottom 901. FIG. 9C is a cross-sectional view of cup bottom 901 along cross-section line 9C—9C of FIG. 9B. FIG. 9D is a detailed view of portion 9D of FIG. 9C. Cup bottom 901 is soft to avoid abrasions and injury to the fetal head. For example, cup bottom 901 may have a durometer measurement (i.e., a measurement of elasticity) of, for example, Shore A 60 durometer. Inward facing surface 902 is adhered or insert molded against a corresponding outwardly facing lip on cup top 401. The combination of cup top 401 and cup bottom 901 defines a fetal contact cup 400 (FIG. 1). Inner surface 920 (FIG. 9D) of cup bottom 901 and inner surface 420 (FIGS. 4E and 4F) of cup top 401 define a fetal contact chamber with the fetal head during vacuum-assisted deliveries.

Figure 10A:
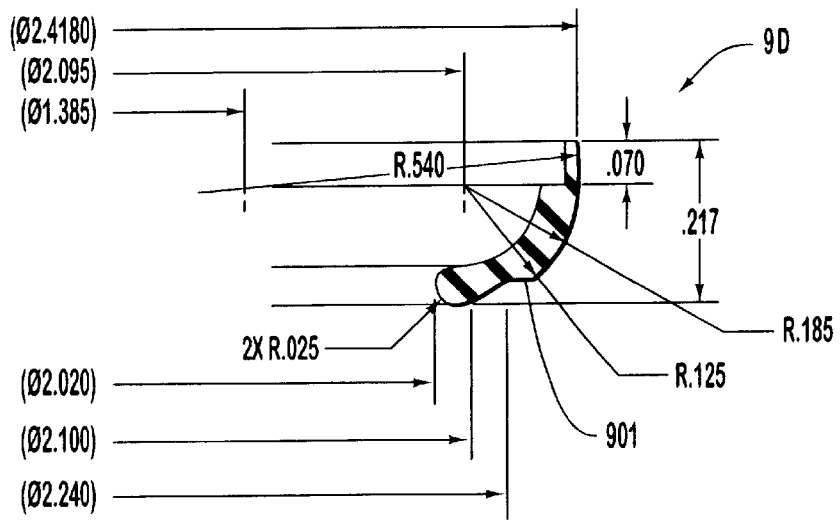
FIG. 10A is a detailed cross-sectional view of a modified portion 9D for use with a lip.
Figure 10B:
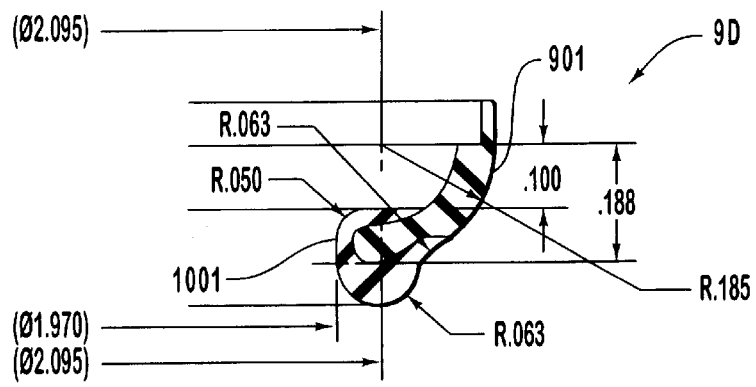
FIG. 10B is a cross-sectional view of portion 9D with the soft lip disposed thereon.
Figure 11:
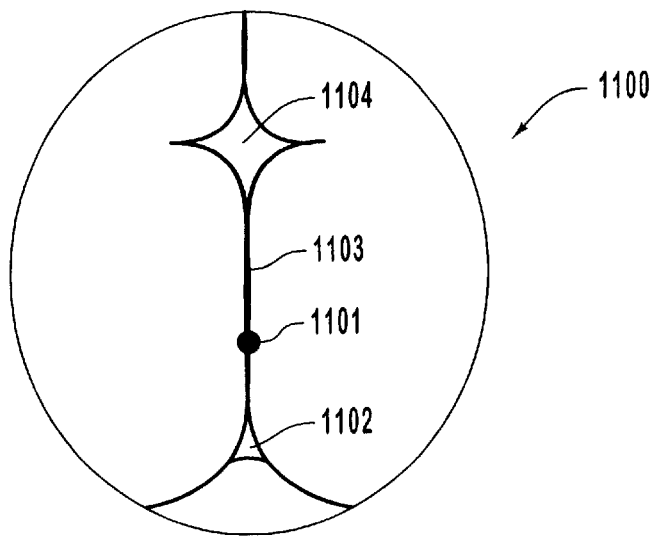
FIG. 11 is a diagram of a fetal head showing the flexion point.
Figure 12:
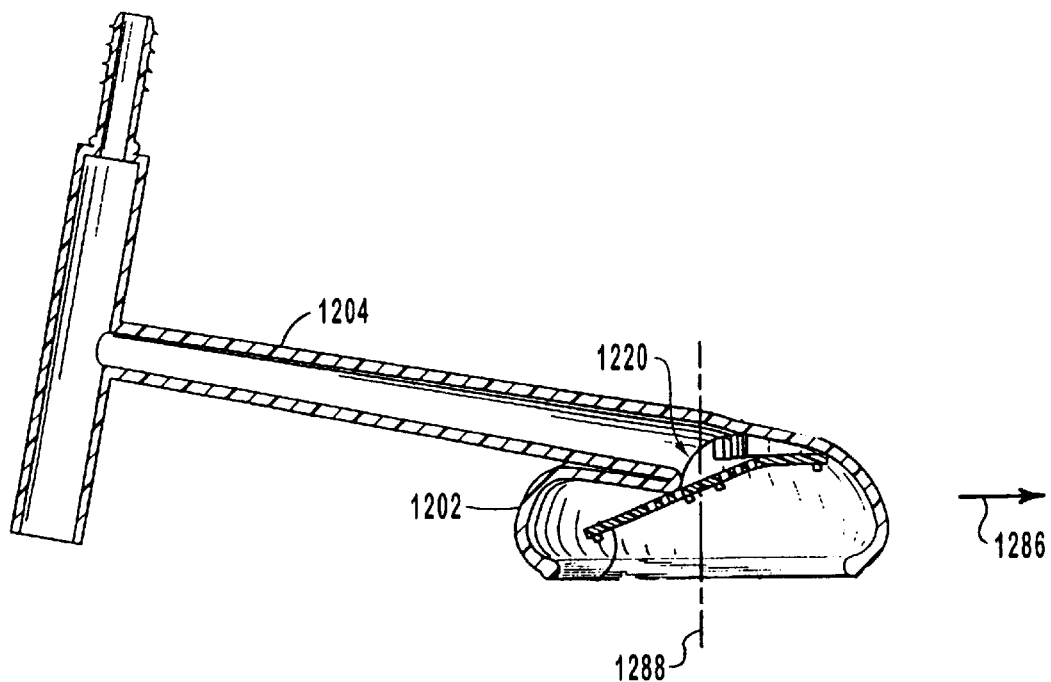
FIGS. 12, 13, 14 and 15 are diagrams of fetal vacuum extractors according to the prior art.
Figure 13:
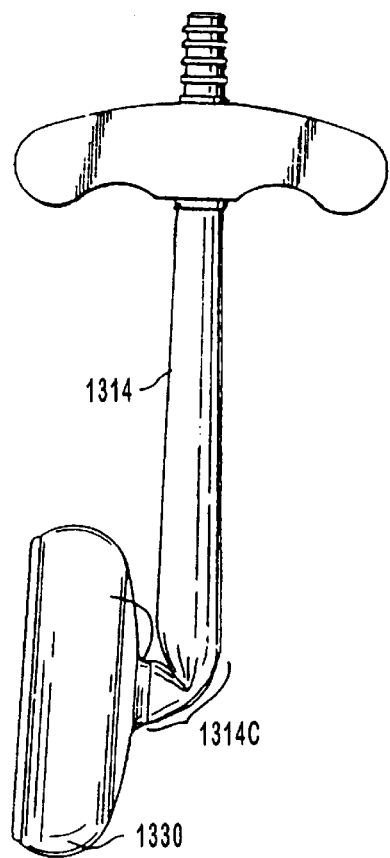
Figure 14:
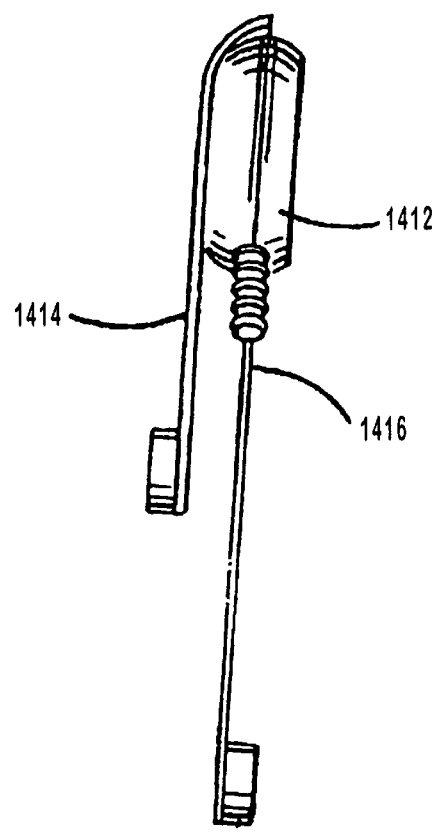
Figure 15:
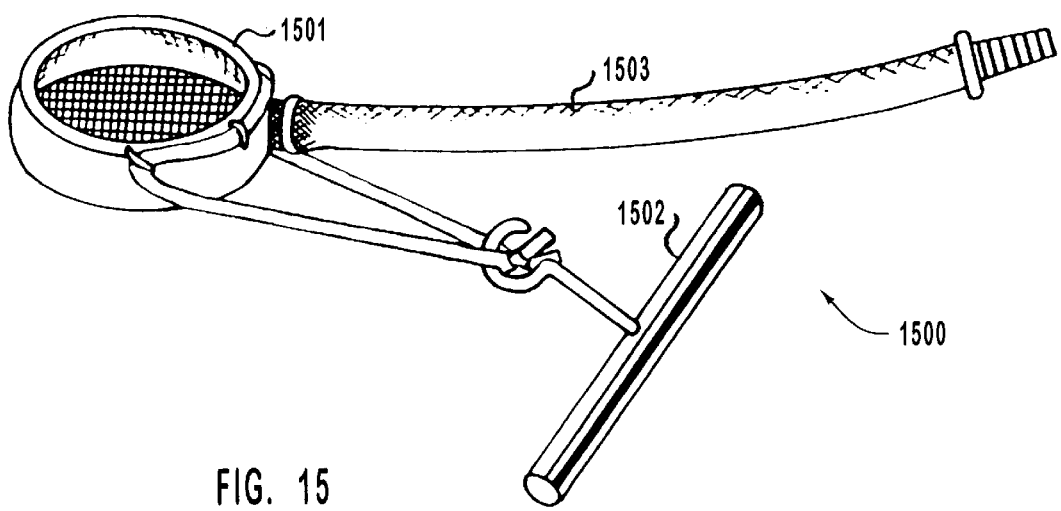

Optionally, cup bottom 901 is formed of a hard material such as polycarbonate. In this case, cup bottom 901 may be modified slightly to have the cross-section shown in FIG. 10A. A soft (e.g., Kraton) lip 1001 may be solvent bonded or insert molded to over portions of cup bottom 901 as seen in FIG. 10B in cross-section. Lip 1001 has an elasticity of, for example, Shore A 35 to 40 durometer.

Figure 9E:
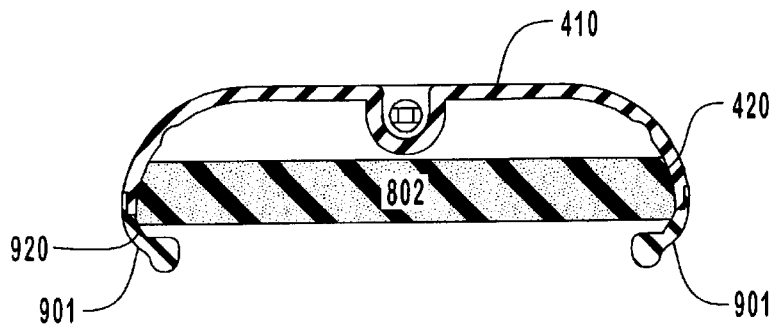
FIG. 9E is a detailed view of a foam filter disposed within the cup top and cup bottom.

Referring to FIG. 1 and FIG. 9E, a filter 802 (e.g., a polyester foam) is inserted into and adhered to inside surface 420 of cup top 401 and inside surface 920 of cup bottom 920. Filter 802 prevents body fluids and tissues from clogging in tube 601, handle 1, and palm chamber 2. Furthermore, filter 802 provides a structural support for the occiput during traction.

Vacuum cup 150 is attached to handle 1 by inserting cup/handle connector 702 of vacuum cup 150 into cup connector 220 of handle 1. The resulting fetal vacuum extractor is shown in exploded view in FIG. 1.

The operation of the fetal vacuum extractor 100 is now described. The fetal vacuum extractor 100 may be used for all vacuum-assisted deliveries. However, the fetal vacuum extractor 100 is particularly useful when the baby is in the high occipitoposterior or high occipitolateral positions at the time of applying vacuum cup 150 since vacuum cup 150 is highly maneuverable between the occiput and the birth canal wall.

Before vaginal insertion, vacuum cup 150, with the pump 120 attached, is placed in the insertion position shown in FIG. 8A. Although not shown in FIG. 8A, the cup bottom 901 and filter 802 are also attached to cup top 401 as described above. In the insertion position, the fetal contact cup 400 (FIG. 1) has a low insertion profile. The distance from the bottom of cup bottom 901 and the top of cup top 401 is, for example, less than one inch. Due to this low profile, fetal contact cup 400 (FIG. 1) may be easily inserted into the birth canal and the center of the fetal contact cup 400 may be more easily positioned on the flexion point even when the fetus is positioned high occipitoposterier or high occipitolateral.

After placement of fetal contact cup 400 (FIG. 1) over the flexion point, a vacuum is applied by, for example, hand pumping palm chamber 2 against handle 1. The fetal scalp is pulled by the vacuum into the fetal contact cup 400 of vacuum cup 150. Thus, the vacuum force applied to the fetal scalp allows for traction to be applied. If enough vacuum is applied, the fetal scalp stretches outwards over the undercutting cup bottom 901 as the fetal scalp is pulled into the fetal contact cup 400. Thus, vacuum cup 150 is coupled to the fetal scalp with mechanical forces as well when a vacuum is applied.

The initial traction is oblique compared to a line perpendicular to the fetal contact cup 400 (i.e., along the z-direction). However, as the occiput is drawn towards the traction direction, finger grip 701 is drawn out of groove 411 and the vacuum cup 150 assumes the traction position shown in FIG. 8B.

The traction force is relatively strong and, under normal circumstances, might stretch tube 601. However, the tensile stretching of tube 601, if any, is contained within the elastic range because cable 501 limits the strain of tube 601.

Thus, fetal vacuum extractor 100 is relatively easily applied onto the flexion point of even malpresenting fetuses. Furthermore, as traction is applied, the fetal contact cup 400 turns relative to tube 601 and traction is efficiently applied perpendicular to the occiput surface. Thus, unlike conventional fetal vacuum extractors used for malpresenting fetuses, the conversion between the insertion position and the traction position requires no special effort by the operator. All that is required is for the operator to apply traction in the proper direction of the birth canal and maintain the vacuum.

Also, only a relatively small amount of material (i.e., a thin tube 601 and the fetal contact cup 400) is inserted into the birth canal thereby causing less maternal discomfort and increased maneuverability in the birth canal. As another advantage, the fluid capacity or volume of the fetal vacuum extractor 100 is relatively low due to the thin diameter of tube 601, and the relatively compact fetal contact cup 400. Thus, the pumping energy needed to draw a vacuum is reduced.

In this description and in the claims, the expression "fluidly attached" is used. A first object is fluidly attached to a second object if the first object can receive fluid from and/or can channel fluid to the second object. This fluid attachment may be direct or may have intermediate fluid channeling components. "Fluidly attachable" means capable of being fluidly attached. "Coupled" means directly attached, or indirectly attached through intermediary support members. "Couplable" means structured to be able to be coupled. "Tube" means any conduit for channeling fluid whether of variable or fixed diameter.

While the maneuverable vacuum cup of the present invention is described with respect to a specific embodiment, this embodiment is illustrative only, and not limiting. Various modifications and substitutions will be obvious to one skilled in the art as being within the scope of the invention.

For example, FIGS. 4A to 4G, 7A, 7B, 9A to 9D and 10A to 10D include various detailed dimension markings that illustrate just one embodiment of the invention. These dimensions may be altered in keeping with the present invention, and thus are not limiting. Furthermore, fetal vacuum extractor is described as having components made of specific materials. Various material substitution may be made consistent with the present invention.

In the above description, a specific configuration of vacuum cup 150 is described. However, various modification may be made within the scope of the invention. For example, although a finger grip 701 of given dimensions is described, finger grip 701 may be altered with a corresponding alteration in the dimensions of groove 411. Although finger grip 701 is useful for insertion of vacuum cup 150, finger grip 701 may even be eliminated completely such that tube 601 itself fits snugly inside groove 411.

The snug fit between finger grip 701 and groove 411 is provided so that vacuum cup 150 remains in the insertion position until traction is applied. However, although this snug fit is useful, the snug fit is not essential to the present invention. Without a snug fit, the user would need to press the finger grip 701 and cup top 401 together during insertion.

A specific low-profile fetal contact cup 400 is described as having groove 411. Various configurations of groove 411 are possible. It is even possible for there to be no groove 411 such that tube 601 protrudes perpendicularly from cup top 401. In this case, the profile of the fetal contact cup is greater than the embodiment described above since the tube 601 extends out from cup top 401. However, this profile would still be lower than conventional fetal vacuum cups due to the small diameter of tube 601. Thus the specific contact cup configuration described above is not essential to the present invention.

Although cable 501 is described above as providing structural support for tube 601 during traction, other types of structural support members may also suffice. Structural supports may be, for example, embedded within or provided on the outside of the walls of tube 601. If sufficiently strong materials are used, tube 601 may not need structural support and thus cable 501 is not essential to the present invention. For example, the walls of tube 601 may be extruded to have a strong wire or nylon braided weave.

Wire 501 is described as being coupled to handle 1 using a crimp 801 and a cup/handle connector 702. Though this coupling assembly allows for easy assembly, other coupling structures are possible as desired.

Thus, the present invention is defined by the following claims.

We claim:

1. A fetal vacuum cup comprising:
    a fetal contact cup having an inside surface, wherein the inside surface defines a fetal contact chamber with a fetal head when the fetal contact cup is applied to the fetal head; and
    a tube comprising a first end fluidly attachable to a vacuum source, the first end of the tube rigidly couplable to a handle, the tube further comprising a second end fluidly attached to the fetal contact cup, wherein the fetal contact cup comprises a cup top having an outside surface that defines a recess aligned in the same direction as the second end of the tube, wherein the tube fits within the recess.

2. The apparatus of claim 1, wherein the tube comprises a finger grip sized to snuggly fit within the recess when compressed, wherein the finger grip remains within the recess unless traction is applied to the fetal contact cup via the tube, wherein the finger grip is sized to allow fingers of an operator to grasp the finger grip for controlling movement of the fetal contact cup.

3. The apparatus of claim 1, wherein the fetal vacuum cup comprises part of a fetal vacuum extractor, the fetal vacuum extractor further comprising:
    the handle, wherein the first end of the tube is coupled to the handle.

4. The apparatus of claim 3, further comprising a vacuum indicator disposed within the handle, the vacuum indicator comprising a piston configured to slide within the handle according to a magnitude of a vacuum within the handle, a magnet being rigidly coupled to the piston, the handle further comprising a viewable slider slidably coupled to a main grip of the handle, wherein the viewable slider is magnetically coupled to the magnet such that the viewable slider moves as the magnet moves, wherein the magnitude of the vacuum within the handle is represented by a position of the viewable slider.

5. A fetal vacuum cup comprising:
    a fetal contact cup having an inside surface, wherein the inside surface defines a fetal contact chamber with a fetal head when the fetal contact cup is applied to the fetal head; and
    a tube comprising a first end fluidly attachable to a vacuum source, the first end of the tube rigidly couplable to a handle, the tube further comprising a second end fluidly attached to the fetal contact cup, wherein the fetal contact cup comprises:
        a rigid cup top coupled to the tube; and a relatively soft cup bottom for contacting the fetal head, wherein the relatively soft cup bottom is non-outwardly flaring below the side of the rigid cup top and has a rounded end for contacting the fetal head.

6. A fetal vacuum cup comprising:
    a fetal contact cup having an inside surface, wherein the inside surface defines a fetal contact chamber with a fetal head when the fetal contact cup is applied to the fetal head; and
    a tube comprising a first end fluidly attachable to a vacuum source, the first end of the tube rigidly couplable to a handle, the tube further comprising a second end fluidly attached to the fetal contact cup, wherein a marker is located on the tube for indicating proper positioning of the fetal contact cup and for indicating fetal progress through the birth canal.

7. A fetal vacuum cup comprising:
    a fetal contact cup having an inside surface, wherein the inside surface defines a fetal contact chamber with a fetal head when the fetal contact cup is applied to the fetal head;
    a tube comprising a first end fluidly attachable to a vacuum source, the first end of the tube rigidly couplable to a handle, the tube further comprising a second end fluidly attached to the fetal contact cup; and
    a pulling member traversing the length of the tube, wherein the pulling member is in tension when the handle is pulled relative to the fetal contact cup.

8. The fetal vacuum cup of claim 7, wherein the pulling member comprises a cable threaded through the tube.

9. The apparatus of claim 7, wherein the average outside diameter of the tube is less than 200 mils.

10. The apparatus of claim 9, wherein the average outside diameter of the tube is less than 150 mils.

11. The apparatus of claim 9, wherein the fetal contact cup comprises a rigid cup top having an outside surface that defines a recess, wherein the tube fits within the recess.

12. The apparatus of claim 11, wherein the tube comprises a finger grip sized to fit within the recess when compressed, wherein the finger grip remains within the recess unless traction is applied to the fetal contact cup via the tube.

13. The apparatus of claim 11, wherein the fetal contact cup comprises:

a rigid cup top coupled to the tube; and a cup bottom comprising a relatively soft lip for contacting the fetal head.

14. The apparatus of claim 13, wherein the rigid cup top is substantially dome-shaped, wherein the cup bottom undercuts the cup top, and wherein the cup bottom further comprises a rigid portion coupling the soft lip to the cup top.

* * * * *